US010366780B2

(12) United States Patent
Dorsett et al.

(10) Patent No.: US 10,366,780 B2
(45) Date of Patent: Jul. 30, 2019

(54) PREDICTIVE PATIENT TO MEDICAL TREATMENT MATCHING SYSTEM AND METHOD

(71) Applicant: Elligo Health Research, Inc., Austin, TX (US)

(72) Inventors: Thomas Dorsett, Austin, TX (US); Tushar Jain, Austin, TX (US)

(73) Assignee: ELLIGO HEALTH RESEARCH, INC., Austin, TX (US)

( * ) Notice: Subject to any disclaimer, the term of this patent is extended or adjusted under 35 U.S.C. 154(b) by 1007 days.

(21) Appl. No.: 14/162,743

(22) Filed: Jan. 24, 2014

(65) Prior Publication Data

US 2015/0213234 A1 Jul. 30, 2015

(51) Int. Cl.
G16H 10/20 (2018.01)

(52) U.S. Cl.
CPC .................. *G16H 10/20* (2018.01)

(58) Field of Classification Search
CPC .......... G06F 19/36; G06F 19/322–327; G06Q 50/22–25; G06H 20/00; G16H 10/20
See application file for complete search history.

(56) References Cited

U.S. PATENT DOCUMENTS

| 5,111,395 A | 5/1992 | Smith et al. |
| 5,995,939 A | 11/1999 | Berman et al. |
| 6,032,119 A | 2/2000 | Brown et al. |
| 6,915,266 B1 | 7/2005 | Saeed et al. |

| 2002/0002474 A1 | 1/2002 | Michelson et al. |
| 2002/0099570 A1 | 7/2002 | Knight |
| 2002/0133502 A1 | 9/2002 | Rosenthal et al. |

(Continued)

FOREIGN PATENT DOCUMENTS

| WO | WO 01/82173 | 11/2001 |
| WO | WO 02/17770 | 3/2002 |
| WO | WO 02/37213 | 5/2002 |

OTHER PUBLICATIONS

International Searching Authority, Internal Search Report and Written Opinion, International Application No. PCT/US2015/012919, dated Apr. 28, 2015.

*Primary Examiner* — Sheetal R Paulson
(74) *Attorney, Agent, or Firm* — Matheson Keys & Kordzik PLLC; Kelly Kordzik (57) ABSTRACT

A predictive system and method for using a physician's existing patient database to more effectively and efficiently identify potential candidates for medical treatments or clinical research trials. The system and method includes an automated three-tiered qualification process using information about a specific medical treatment received from a company looking for potential candidates for the medical treatment wherein potential candidates are initially prequalified by comparing the information about the medical treatment to the information contained in a physician's patient database. The potential candidates that are identified by the first tier of the qualification process then answer additional questions from a patient screening survey. Finally, additional questions from a physician consultation questionnaire are completed by the referring physician's office. If a potential candidate passes all three tiers of qualification, the potential candidate is then passed to the company looking for potential candidates for the medical treatment.

20 Claims, 2 Drawing Sheets

(56) References Cited

U.S. PATENT DOCUMENTS

| | | |
|---|---|---|
| 2003/0039362 A1 | 2/2003 | Califano et al. |
| 2003/0130871 A1 | 7/2003 | Rao et al. |
| 2003/0208378 A1 | 11/2003 | Thangaraj et al. |
| 2004/0078238 A1 | 4/2004 | Thomas et al. |
| 2004/0172293 A1 | 9/2004 | Bruschi et al. |
| 2005/0182665 A1 | 8/2005 | Abraham-Fuchs et al. |
| 2007/0067189 A1* | 3/2007 | Boris et al. ............ 705/3 |
| 2007/0143148 A1 | 6/2007 | Kol et al. |
| 2007/0250347 A1 | 10/2007 | Abraham-Fuchs et al. |
| 2010/0169115 A1* | 7/2010 | Tamis et al. ............ 705/2 |
| 2012/0084100 A1 | 4/2012 | Tilles et al. |
| 2012/0316898 A1 | 12/2012 | Levitt et al. |

\* cited by examiner

PREDICTIVE PATIENT TO MEDICAL TREATMENT MATCHING SYSTEM AND METHOD

BACKGROUND OF THE INVENTION

1. Field of the Invention

The present invention relates generally to the field of healthcare. More specifically, the present invention relates to a predictive system and method for using a physician's existing client base to more effectively and efficiently identify potential candidates for new or little known medical treatments or clinical research trials.

Within the health care industry, and in particular within the field of clinical research, there is a need for a more effective process to identify and place candidates for clinical research trials to try new and improved products and services, including but not limited to new and/or potentially improved pharmaceutical products, medical devices, and procedures. Clinical trials are typically research studies conducted on volunteers to study the effectiveness of a new or improved medical product or service. The sponsor is typically the manufacturer of a drug or medical device and funds the clinical study, often as part of its FDA approval process. Sponsors can include pharmaceutical companies, clinical research organizations, medical device manufacturers, and site management organizations. An investigator is typically a research physician or group of physicians that actually conducts the clinical trial for the sponsor.

Volunteers that participate in a given clinical trial must meet certain criteria established by the sponsor and/or the investigator. Sample criteria may include type of disease, previous treatment history, other medical conditions that may be affected by participation in the study, age, and gender. Whether or not certain criteria are inclusive or exclusive typically depends on the nature of the clinical trial itself. Volunteers are carefully advised of the details of the clinical trial to ensure that they aware of both the positive potential impacts of participating in the study as well as the negative potential impacts of participating in the study.

Volunteers may participate in the clinical trial for various reasons, such as an opportunity to gain access to treatments that they otherwise could not because they are not on the market, have not been approved by the FDA, or could not afford, they may be motivated by the desire to contribute to medical research, or may simply be motivated to participate because of the money they are paid to participate.

It has been reported that the cost to bring a new drug to market can be one billion dollars. Because only approximately one in ten drugs are ever approved for market by the FDA, adjusting that number for current failure rates results in an estimated four billion dollars in research spent for every drug that is approved. A single clinical trial can cost one hundred million dollars. As a result, pharmaceutical companies must employ more effective and efficient methods of conducting clinical trials.

According to a Tufts University study, a pharmaceutical company can lose over a million dollars per day in lost drug sales for each day a clinical study is not complete. The clinical trial process can be slow and one of the main reasons is the time it takes to find a suitable population for the study. Sufficiently populating a clinical trial often takes more than a year and represents more than 25% of the entire length of the study lifecycle.

In addition to clinical trials, pharmaceutical companies, medical device manufacturers, and the like are constantly developing, improving, and discovering new medical treatments for medical conditions that may not be well known for the treatment of a certain condition. For example, some pharmaceutical products are not well known within the medical community because they are very expensive and, as such, are seldom used. However, there are often occasions when these drugs are highly effective for a certain condition but the medical provider is not familiar with the drug. There may be other instances where a medical device can be used to treat a condition but the device is not well known because FDA approval was not required. The medical device manufacturers have a need to identify potential candidates for its device and make the medical providers aware of its potential use.

2. Description of Related Art

A review of related art identifies various techniques that are currently used to identify suitable potential candidates for new or little known medical treatments or to participate in a clinical trial. The company or investigator may place advertisements, using various media such as newspaper, radio commercials, billboards, interact advertising, and the like, to find or solicit potential candidates. Information materials may also be given to specialist physicians for a related area of the medical treatment or clinical trial or to support groups for a specific condition. Success rates using these traditional methods are typically poor due to the inability to reach a large pool of potentially qualified candidates, and those that may be interested and do respond often do not meet the criteria to participate in the study.

Physicians are also often involved in referring patients to clinical trials. However, successful referral rates from physicians are not optimal either because physicians are usually extremely busy and have little time to study available clinical trials and assure their patients meet the necessary criteria for participation in a clinical trial.

In order to improve upon these traditional methods of identifying potential candidates for new or little known medical treatments or clinical research trials, various business efficiencies have been employed. For clinical trials, some use an online web-based system to screen potential candidates and match those candidates with various clinical research trials that the user may be qualified for. However, while these systems do improve upon the traditional methods to identify and recruit potential candidates for clinical research trials, these internet sites typically rely on information from a single source that does not have access to all information.

For example, some of these systems are directed to investigators and their database of patients they have worked with in the past. However, the investigator's information for its past patients is going to be stale and only specific to the clinical research trial that a patient may have been involved with in the past.

Other existing systems have the potential candidate complete a patient questionnaire to build a profile that will be compared against specific criteria for a clinical research trial. However, the potential candidates themselves will not know specific medical information such as the calcium level of a specific lab they had completed. This information is often kept with the physician.

Still other systems are directed toward physicians who are specialists in the area that is relevant to the clinical trial, such as an oncologist for clinical research trials involving cancer patients. These physicians typically depend on referrals from primary care physicians after a patient has been diagnosed, are treating patients with the latest technology that they have, and are extremely busy and have little time to fill out patient questionnaires. Further, these physicians cannot answer candidate specific questions such as whether a candidate plans on getting pregnant in the next six months.

A need exists, therefore, for an efficient and effective method and system to identify qualified potential candidates for new or little known medical treatments or clinical trials. A need also exists for a method and system of providing pertinent information related to the identified potential candidate such as answers to questions specific to the medical treatment or clinical trial, general demographic information, medical history, and medical records. A need also exists for a method and system to provide a more targeted search that will result in a higher percentage of qualified potential candidates for a specific medical treatment or clinical trial. The presented invention and embodiments thereof satisfy these needs.

All references cited herein are incorporated by reference to the maximum extent allowable by law. To the extent a reference may not be fully incorporated herein, it is incorporated by reference for background purposes and indicative of the knowledge of one of ordinary skill in the art.

BRIEF SUMMARY OF THE INVENTION

The problems presented are solved by the systems and methods of the present invention. In accordance with one embodiment of the present invention, a predictive system and method for using a physician's existing client base to more effectively and efficiently identify potential candidates for a specific medical treatment is provided. More specifically, the invention is directed to a method that includes a three-tiered qualification process that may be automated using information about a specific medical treatment, which may include a clinical research trial, received from a company looking for potential candidates for the medical treatment. Potential candidates are initially prequalified by comparing the information about the medical treatment received from the company looking for potential candidates to the information contained in a physician's patient database. The potential candidates that are identified as likely candidates by the first tier of the qualification process then answer additional questions from a patient screening survey. The answers from the patient screening survey are then scored and those candidates that meet the required score move to the third tier of the qualification process. Additional questions from a physician consultation questionnaire about the potential candidates that remain are then provided to and answered by the potential candidates' referring physician's office. If a potential candidate passes through all three tiers of qualification, the potential candidate is then passed to the company looking for potential candidates for the medical treatment or clinical trial. This first embodiment of the present invention responds to the need to more effectively identify potential candidates for new or little known medical treatments or clinical research trials.

In accordance with another embodiment of the present invention, the method described above can be embodied in computer executable software code. This embodiment of the present invention responds to the need to more efficiently identify potential candidates for new or little known medical treatments or clinical research trials.

In accordance with another embodiment of the present invention, the method and computer executable software code described above can be combined with a server and its components, a company's system, a physician's system that includes a patient database, and a patient's system, all connected to a network, to provide a system for identifying potential candidates for a specific medical treatment, which may include a clinical research trial. This embodiment of the present invention responds to the need to more effectively and efficiently identify potential candidates for new or little known medical treatments or clinical research trials.

Other objects, features, and advantages of the present invention will become apparent with reference to the drawings and detailed description that follow.

DETAILED DESCRIPTION OF THE PREFERRED EMBODIMENT

All references cited herein are incorporated by reference to the maximum extent allowable by law. To the extent a reference may not be fully incorporated herein, it is incorporated by reference for background purposes and indicative of the knowledge of one of ordinary skill in the art.

In the following detailed description of the preferred embodiments, reference may be made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense.

The present disclosure relates to a predictive system and method for using a physician's existing patient database to more effectively and efficiently identify potential candidates for a specific medical treatment. In the context of the present invention, a medical treatment includes any indication of a substance or technique used in treating a health-related condition, including but not limited to new or little known medical procedures or pharmaceutical products, clinical research trials, new indications for existing pharmaceutical products, new biologics, orphan drugs, new surgical treatments, new medical devices, research on the effectiveness of a vitamin supplement, and the like. The method includes a three-tiered qualification process using information about a specific medical treatment and (1) comparing that information to the patient records contained in a referring physician's patient database, (2) for those potential candidates that pass the first tier of the qualification process, receiving additional information directly from the potential candidate, and (3) for those potential candidates that have passed the first two tiers of the qualification process, receiving additional information from the potential candidate's referring physician's office.

The information about a specific medical treatment is received from a company looking for potential candidates for the medical treatment. In the context of the present invention, a company includes any entity, including organizations and individuals, looking for potential candidates for a medical treatment, including but not limited to contract research organizations, pharmaceutical and biotechnology manufacturers, medical device manufacturers, healthcare researchers, and the like. Potential candidates are initially prequalified by comparing the information about the medical treatment received from the company looking for potential candidates to the information contained in a physician's patient database. The potential candidates that are identified as likely candidates by the first tier of the qualification process then answer additional questions from a patient screening survey. The answers from the patient screening survey are then scored and those candidates that meet the required score move to the third tier of the qualification process. Additional questions from a physician consultation questionnaire about the potential candidates that remain are then provided to and answered by the potential candidates' referring physician's office. If a potential candidate passes through all three tiers of qualification, the potential candidate is then referred to the company looking for potential candidates for the medical treatment.

Computer executable software code written according to the method above provides another embodiment of the present invention.

The method and computer executable software code can be combined with a server and its components, a company's system, a physician's system that includes a patient database, and a patient's system, all connected to a network, to provide another embodiment of the present invention.

Figure 1:
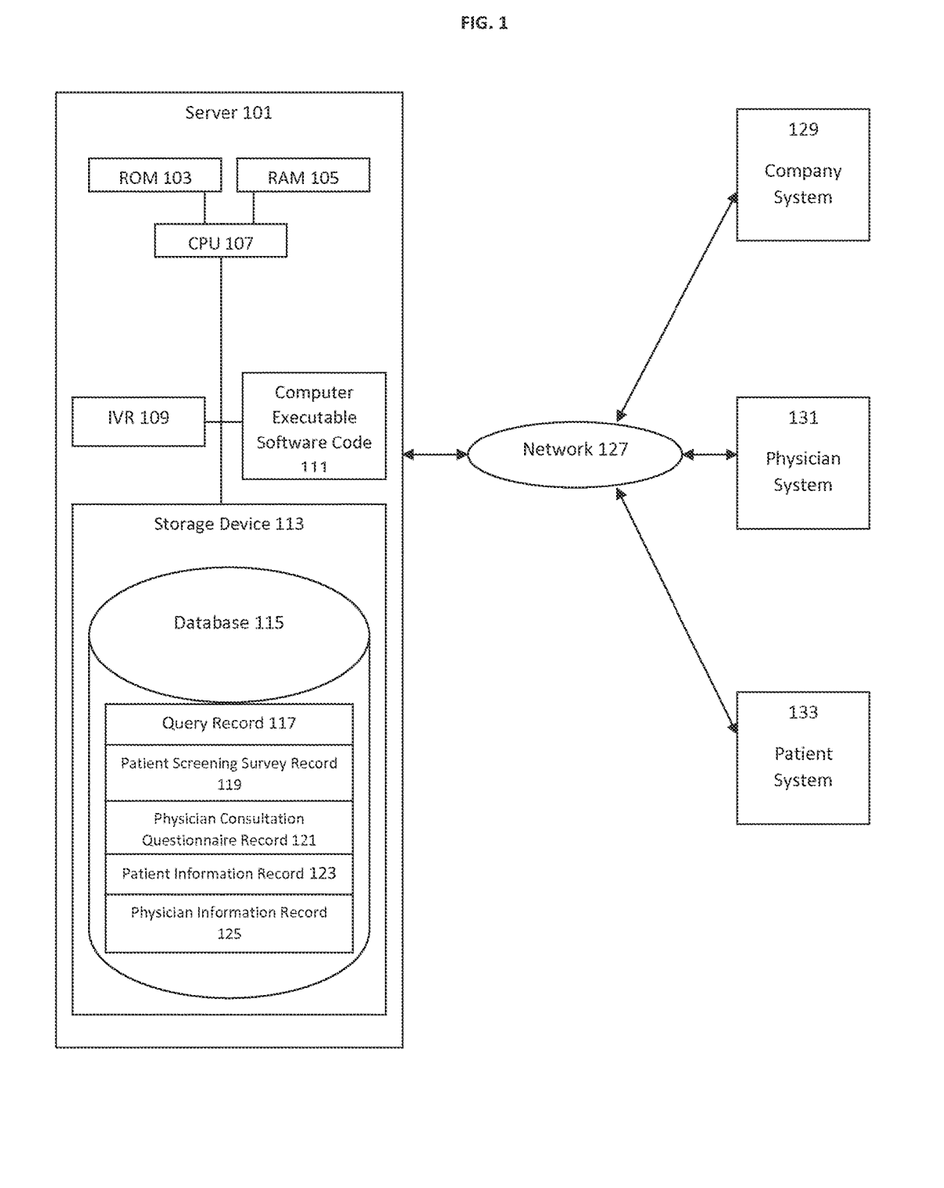
FIG. 1 is a block diagram illustrating an exemplary system in accordance with an illustrative embodiment of the present invention.
Figure 2:
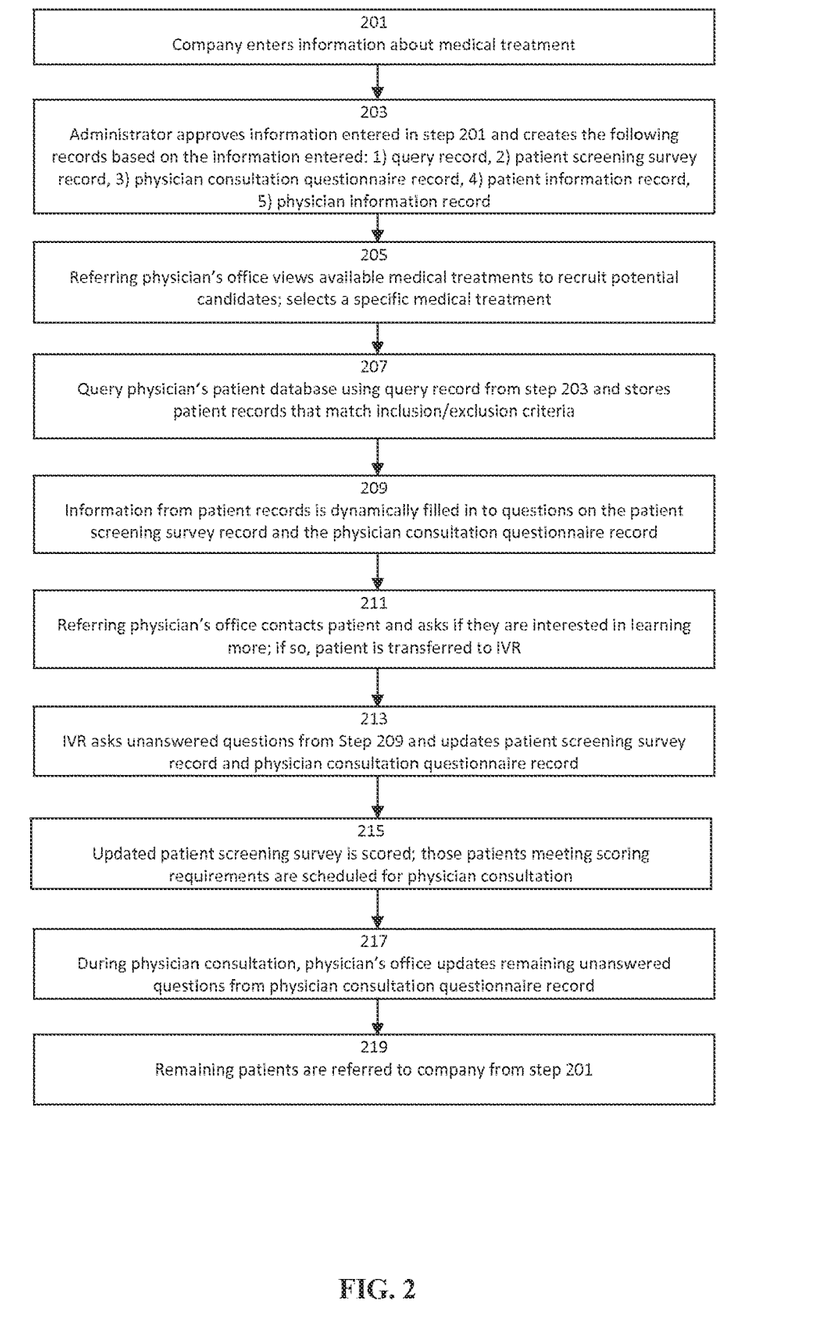
FIG. 2 is a flowchart illustrating an exemplary method in accordance with an illustrative embodiment of the present invention

Referring to the figures, FIG. 1 is a block diagram illustrating an exemplary system in accordance with an illustrative embodiment of the present invention. FIG. 2 is a flowchart illustrating an exemplary method in accordance with an illustrative embodiment of the present invention.

Describing an embodiment of the present invention as a system illustrates both the systems and methods to more effectively and efficiently identify potential candidates for a specific medical treatment of the present invention. A server 101 contains read-only memory 103 and random access memory 105 as well as a central processing unit 107. An interactive voice response system 109 and computer executable software code 111, as well as storage device 113, reside on the server 101. A database 115 is stored on the storage device 113 and contains certain records relating to a specific medical treatment. The records include a medical treatment specific query record 117, a medical treatment specific patient screening survey record 119, a medical treatment specific physician consultation questionnaire record 121, a medical treatment specific patient information record 123, and a medical treatment specific physician information record 125. The server 101 is connected to a network 127.

In step 201, a company looking for potential candidates for a specific medical treatment connects to the server 101 through the network 127 using the company's system 129. The medical treatment could be any medical treatment for which a company is looking for potential patients, such as a new indication of an existing pharmaceutical product, a new medical device, a new surgical treatment, a clinical trial for a new pharmaceutical product, medical device, or medical treatment, or the like. The computer executable software code 111 guides the company to enter specified information about the medical treatment that the company is recruiting potential candidates for. The specified information could include the name of the condition to be treated, an Institutional Review Board approved description of the medical treatment, inclusion and exclusion criteria for the potential candidates, patient compensation, referral compensation, information about the specific medical treatment for the referring physicians, geographic locations of available sites for the medical treatment, and the like.

In step 203, the administrator of the server 101 accesses the information about the specific medical treatment that has been input by the company and, after reviewing the information for completeness and approving the information, launches computer executable software code 111 that automatically creates the following records based on the information received from the company: a medical treatment specific query record 117, a medical treatment specific patient screening survey record 119, a medical treatment specific physician consultation questionnaire record 121, a medical treatment specific patient information record 123, and a medical treatment specific physician information record 125. These records are stored in the database 115 on the server 101. The computer executable software code 111 applies a score to each of the possible answers to the patient screening survey.

In step 205, a referring physician's office connects to the server 101 through the network 127 using the referring physician's system 131. The referring physician's system 131 includes the physician's patient database. The referring physician then browses the physician information records 125 to search for a specific medical treatment to recruit for. The physician information records 125 could including location, specialties, compensation, whether the physician has participated in recruiting potential candidates for a related medical treatment or company, benefits for said potential patient, cost of said medical treatment, whether said medical treatment is new or a new indication of a known medical treatment and the like. The computer executable software code 111 allows the referring physician to sort the available medical treatments based on the information in the physician information records 125. Once the referring physician finds a specific medical treatment that he is interested in recruiting potential patients for, the referring physician selects the specific medical treatment. By collecting and sorting information about the specific medical treatment the physician is only shown medical treatments that he is likely to be interested in and is eligible to recruit for. In another embodiment of the present invention, this matching algorithm can be used to recommend medical treatments to referring physicians on a weekly basis.

Step 207 begins the first of three tiers in the qualification system and method of identifying potential candidates and/or patients for a medical treatment. In step 207, after the referring physician's office selects a specific medical treatment an applet is launched that runs in the browser of the referring physician's system 131. The applet connects to the patient database residing on the referring physician's system 131 and accesses the medical treatment specific query record 117 relating to the specific medical treatment that the referring physician's office has selected. Using the medical treatment specific query record 117, the applet runs the query on the referring physician's patient database and compares the patient records in the patient database with the inclusion and exclusion criteria for the specific medical treatment contained in the medical treatment specific query 117. The applet then returns the patient records from the patient database that match the inclusion and exclusion criteria through the network 127 to the server 101 and stores the patient records in the database 115.

In another embodiment of the present invention, there may be patients from the physician's patient database that have already been asked whether they want to be contacted about participating in new medical treatments. If the patient has previously declined, this can be noted in the patient record on the database so that, if the patient is a match for a future medical treatment, even though the patient is identified they will not be contacted with regards to future medical treatments.

In another embodiment of the present invention, after the referring physician's office selects a specific medical treatment, rather than launching an applet that runs in the browser of the referring physician's system 131, a secure connection is made between the patient database residing on the referring physician's system 131 and the server 101. The computer executable software code 111 then accesses the medical treatment specific query record 117 and runs the query on the referring physician's patient database, storing those patient records that match the inclusion and exclusion criteria on the server 101 in the database 115.

In step 209, the computer executable software code 111 compares information obtained from the patient record of the referring physician's patient database with questions from the medical treatment specific patient screening survey record 119 and the medical treatment specific physician consultation questionnaire record 121. The Computer executable software code 111 then dynamically completes those fields in the medical treatment specific patient screening survey record 119 and the medical treatment specific physician consultation questionnaire record 121 that match information from the patient record.

In step 211, the referring physician's office accesses the server 101 over the network 127 using the referring physician's system 131 and is presented with the patients associated with the patient records stored on the server 101 that have passed the first tier of the qualification process from the referring physician's patient database. The referring physician's office then contacts a patient to inquire whether the patient is interested in learning more about the specific medical treatment for which the patient has passed the first tier of the qualification process. If the patient is interested in continuing in the qualification process, the referring physician's office then transfers the patient to an interactive voice response system 109. If the patient declines, the referring physician's office updates the patient record on the server 101. The patient record associated with this patient will contain a record so that if this patient qualifies for a specific medical treatment in the future, the patient record will not be presented to the referring physician's office.

Step 213 begins the second of three tiers in the qualification system and method of identifying potential candidates and/or patients for a medical treatment. In step 213, once the patient has been connected with the interactive voice response system 109, the patient completes the medical treatment specific patient screening survey. The interactive voice response system 109 accesses the medical treatment specific patient screening survey record 119 and asks the patient all questions that remain unanswered, or unmatched from the dynamically completed information from step 209. As the patient answers questions through the interactive voice response system 109, the interactive voice response system 109 fills in the unanswered/unmatched questions on the medical treatment specific patient screening survey record 119 and the medical treatment specific physician consultation questionnaire record 121 and stores these updated records in the database 115 on the server 101.

In another embodiment of the present invention, instead of transferring the patient to an interactive voice response system 109 connected to the server 101, the referring physician's office directs the patient to a website hosted on the server 101. The patient connects to the website hosted on the server 101 through the network 127 using a browser on the patient's system 133. The patient is then presented all of the questions that remain unanswered from the medical treatment specific patient screening survey record 119, or the unmatched fields from the dynamically completed information from step 209. The patient then answers the unanswered/unmatched questions and the answers are sent through the network 127 to the server 101, where the medical treatment specific patient screening survey record 119 and the medical treatment specific physician consultation questionnaire record 121 are updated in the database 115 and stored on the server 101.

In step 215, the computer executable software code 111 then scores the updated medical treatment specific patient screening survey record 119 and those patients that meet the predetermined required score are scheduled for a consultation with the referring physician's office.

In another embodiment of the present invention, those patients that do not meet the predetermined required score are notified that they did not meet the qualifications for the specific medical treatment. This may be done by one or more methods, including notifying the patient through the interactive voice response system 109, sending the patient an email, sending the patient a letter, having the physician's office contact the patient, and the like.

Step 217 begins the third of three tiers in the qualification system and method of identifying potential candidates and/or patients for a medical treatment. In step 215, when the patient arrives at the referring physician's office for a consultation, the physician or suitable staff member, using the referring physician's system 131, connects to the server 101 over the network 127 and is presented with the medical treatment specific physician consultation questionnaire that is derived from the medical treatment specific physician consultation questionnaire record 121. During the consultation, the physician or suitable staff member views the information that has been completed to date and completes the unanswered questions, or unmatched fields in the medical treatment specific physician consultation questionnaire record 121. The updated answers are then sent to the server 101 and stored in the database 115. This is the opportunity for the physician to enter information which the patient would not know, such as a specific lab test result, and that was not able to be queried because it was not structured data, was a scanned in document, or was not mapped correctly.

In step 219, the computer executable software code 111 then sends the patient record associated with the patients that have passed the three-tiered qualification process to the company looking for potential candidates for the specific medical treatment. Information sent to the company may include the medical treatment specific patient screening survey, medical treatment specific physician consultation questionnaire, as well as a Continuity of Care Document or Continuity of Care Record that contains the patient's medical records. This can potentially save the researcher a lot of money as they will not have to do redundant tests and will have access to the patient's verified medical info.

In another embodiment of the present invention, those patients that have not passed all three tiers of the qualification process are notified that they did not meet the qualifications for the specific medical treatment. This may be done by one or more methods, including notifying the patient by sending the patient an email, sending the patient a letter, having the physician's office contact the patient, and the like.

The primary advantage of the present invention is to more effectively and efficiently identify potential candidates for a medical treatment, which includes clinical research trials, using a three-tiered qualification process.

Another advantage of the present invention is that the three-tiered qualification process collects more information by collecting information from patient records, the patient themselves, as well as ensuring any remaining questions are answered through the physician consultation. The present invention also ensures that the information collected is accurate by involving the patient and the referring physician. The present invention uses a combination of automated query, survey, and questionnaire to gather the information needed and more efficiently and effectively find qualified candidates.

For example, for a specific medical treatment three of the criteria to determine eligibility for a specific medical treatment may be: (1) the patient must be diagnosed with asthma, (2) the patient cannot intend to get pregnant during the course of the treatment, and (3) a free calcium level of no more than 4.8. The patient will know if they have been diagnosed with asthma and the diagnosis can typically be found in the electronic health records from a physician's patient database. However, the physician's patient database is not going to know whether the patient intends on getting pregnant. The present invention solves this by involving the patient in the process and collecting this information directly from the patient. A patient's free calcium level is usually contained in a lab test result, which would not be able to be queried because lab test results are typically stored in PDF documents. Further, a patient is not likely to know their free calcium level. The present invention solves this by involving the referring physician where he can enter this data during the patient consultation.

Another advantage of the present invention is only asking a question from the patient screening survey or the physician consultation questionnaire if the answer has not been collected from some other source, such as from the patient's medical record contained in the physician's patient database or from the patient himself.

Even though many of the examples discussed herein are applications of the present invention in relation to new or little known medical treatments, which includes clinical research trials, the present invention also can be applied to other types of medical treatments, including but not limited to new indications for existing pharmaceutical products, new biologics, orphan drugs, new surgical treatments, new medical devices, research on the effectiveness of a vitamin supplement, and the like.

One skilled in the art will see that the present invention can be applied in many areas where there is a need to more effectively and efficiently identify potential candidates for a specific medical treatment.

It should be apparent from the foregoing that an invention having significant advantages has been provided. While the invention is shown in only a few of its forms, it is not just limited but is susceptible to various changes and modifications without departing from the spirit thereof.

The invention claimed is:

1. A method for matching patients with a specific medical treatment comprising:
receiving specified information about a specific medical treatment from a company looking for potential candidates for said specific medical treatment at a server, wherein said specified information about said specific medical treatment is determined by a software application residing on said server and provided by said company over a network by said company's system;
accessing said specified information about said specific medical treatment on said server by the administrator of said server, wherein said administrator approves said specified information about said specific medical treatment and thereinafter creates a medical treatment specific query record based on said specified information about said specific medical treatment that includes inclusion and exclusion criteria, a medical treatment specific patient screening survey record based on said specified information about said specific medical treatment, a medical treatment specific physician consultation questionnaire record based on said specified information about said specific medical treatment, a medical treatment specific patient information record based on said specified information about said specific medical treatment, and a medical treatment specific physician information record based on said specified information about said specific medical treatment;
browsing said medical treatment specific physician information records using a browser connected to the system of a referring physician's office to connect to said server through said network, wherein said system of a referring physician's office includes a patient database;
selecting at least one said specific medical treatment;
launching an applet from said server, wherein said applet runs in said browser, connects to said patient database, and accesses said medical treatment specific query record relating to said selected medical treatment;
using the medical treatment specific query record, querying said patient database, wherein said applet runs said medical treatment specific query and compares patient records in said patient database with said inclusion and exclusion criteria of said medical treatment specific query, returning said patient records from said patient database that match said inclusion and exclusion criteria of said medical treatment specific query through said network to said server and storing said patient records on said server;
comparing said patient record with said medical treatment specific patient screening survey record and said medical treatment specific physician consultation questionnaire record and completing fields in said medical treatment specific patient screening survey record and said medical treatment specific physician consultation questionnaire record that match information from said patient record;
contacting a patient associated with said patient records stored on said server by accessing said patient records through said network on said system of referring physician's office, wherein said referring physician's office contacts said patient to inquire whether said patient is interested in learning more about said medical treatment, wherein if said patient declines, said patient record is updated by said referring physician's office through said network using said system of referring physician's office, wherein if said patient accepts, said patient is transferred to an interactive voice response system connected to said server;
completing the medical treatment specific patient screening survey, wherein said interactive voice response system accesses said medical treatment specific patient screening survey record and asks said patient unmatched questions from said medical treatment specific patient screening survey, wherein said patient answers said unmatched questions and said answers are sent through said interactive voice response system to said server, wherein said medical treatment specific patient screening survey record and said medical treatment specific physician consultation questionnaire record are updated and stored on said server;

scoring answers in said medical treatment specific patient screening survey record using said software application and scheduling said patient that has a predetermined minimum score for a consultation with said referring physician's office;

completing the medical treatment specific physician consultation questionnaire record, wherein said patient visits said referring physician's office and personnel from said referring physician's office accesses said medical treatment specific physician consultation questionnaire record using a browser connected to said system of said referring physician's office to connect to said server through said network, wherein said personnel completes answers to said medical treatment physician consultation questionnaire and sends those answers to said server using a browser connected to the system of a referring physician's office to connect to said server through said network, wherein said medical treatment specific physician consultation questionnaire record is updated and stored on said server; and sending said patient record to said company looking for potential candidates for said specific medical treatment using said software application.

2. The method according to claim 1 wherein:
said specified information includes the name of the condition to be treated by said specific medical treatment, an Institutional Review Board approved description of said specific medical treatment, inclusion and exclusion criteria for said potential candidates for said specific medical treatment, patient compensation for said potential candidates for said specific medical treatment, information about said specific medical treatment for referring physicians, and available sites for said medical treatment.

3. The method according to claim 1 wherein:
said medical treatment specific physician information record contains information about said specific medical treatment including location, specialties, compensation, whether the physician has participated in recruiting potential candidates for a related medical treatment or company, benefits for said potential patient, cost of said medical treatment, whether said medical treatment is new or a new indication of a known medical treatment, wherein this information can be sorted based on input from said physician to assist in the search of relevant medical treatment specific physician information records.

4. The method according to claim 1 wherein:
in said accessing step, said administrator enables said software application on said server to automatically create said medical treatment specific query record based on said specified information about said specific medical treatment that includes inclusion and exclusion criteria, said medical treatment specific patient screening survey record based on said specified information about said specific medical treatment, said medical treatment specific physician consultation questionnaire record based on said specified information about said specific medical treatment, said medical treatment specific patient information record based on said specified information about said specific medical treatment, and said medical treatment specific physician information record based on said specified information about said specific medical treatment.

5. The method according to claim 1 wherein:
said contacting step is replaced with the following:

contacting a patient associated with said patient records stored on said server by accessing said patient records through said network on said system of referring physician's office, wherein said referring physician's office contacts said patient to inquire whether said patient is interested in learning more about said medical treatment, wherein if said patient declines, said patient record is updated by said referring physician's office through said network using said system of referring physician's office, wherein if said patient accepts, said patient is directed to a website hosted on said server, wherein said patient connects to said website hosted on said server through said network using a browser on said patient's system;

said completing the medical treatment specific patient screening survey step is replaced with the following:

completing the medical treatment specific patient screening survey, wherein said patient is presented through said patient's browser said unmatched questions to said medical treatment specific patient screening survey record, wherein said patient then answers said unmatched questions and the answers are sent through said network to said server, wherein said medical treatment specific patient screening survey record and said medical treatment specific physician consultation questionnaire record are updated and stored on said server.

6. The method according to claim 1 wherein:
said launching step is replaced with the following:
securely connecting said server to said system of a referring physician's office, wherein said software application connects to said patient database and transfers patient records from said patient database to said server;

said using step is replaced with the following:
querying said patient records stored on said server, wherein said software application runs said medical treatment specific query and compares patient records stored on said server with said inclusion and exclusion criteria of said medical treatment specific query.

7. A computer program product stored on a computer readable storage medium, which when executed, performs a method for matching patients with a specific medical treatment, comprising:

receiving at a server specified information about a specific medical treatment from a company looking for potential candidates for said specific medical treatment, wherein said specified information about said specific medical treatment is determined by a predefined form within said computer program product stored on said computer readable storage medium, wherein said specified information is provided by said company over a network by said company's system;

accessing said specified information about said specific medical treatment on said server by an administrator of said server, wherein said administrator approves said specified information about said specific medical treatment using said computer program product stored on said computer readable storage medium and creating a medical treatment specific query record based on said specified information about said specific medical treatment that includes inclusion and exclusion criteria, a medical treatment specific patient screening survey record based on said specified information about said specific medical treatment, a medical treatment specific physician consultation questionnaire record based on said specified information about said specific medical treatment, a medical treatment specific patient information record based on said specified information about said specific medical treatment, and a medical treatment specific physician information record based on said specified information about said specific medical treatment;

browsing said medical treatment specific physician information records using a browser connected to the system of a referring physician's office to connect to said server through said network, wherein said system of said referring physician's office includes a patient database;

launching an applet from said server, wherein said applet runs in said browser, connects to said patient database, and accesses said medical treatment specific query record relating to said specific medical treatment;

using the medical treatment specific query record, querying said patient database, wherein said applet compares patient records in said patient database with said inclusion and exclusion criteria of said specific medical treatment, returning said patient records from said patient database that match said inclusion and exclusion criteria of said specific medical treatment through said network to said server and storing said patient records on said server;

comparing said patient records with said medical treatment specific patient screening survey record and said medical treatment specific physician consultation questionnaire record and completing fields in said medical treatment specific patient screening survey record and said medical treatment specific physician consultation questionnaire record that match information from said patient records;

contacting a patient associated with said patient records stored on said server by accessing said patient records through said network on said system of said referring physician's office, wherein said referring physician's office contacts said patient to inquire whether said patient is interested in learning more about said specific medical treatment, wherein if said patient declines, said patient records are updated by said referring physician's office through said network using said system of said referring physician's office, wherein if said patient accepts, said patient is transferred to an interactive voice response system connected to said server;

completing the medical treatment specific patient screening survey record, wherein said interactive voice response system accesses said medical treatment specific patient screening survey record and asks said patient unmatched questions from said medical treatment specific patient screening survey record, wherein said patient answers said unmatched questions and said answers are sent through said interactive voice response system to said server, wherein said medical treatment specific patient screening survey record and said medical treatment specific physician consultation questionnaire record are updated with said answers and stored on said server;

scoring said answers in said medical treatment specific patient screening survey record using said computer program product stored on said computer readable storage medium and scheduling said patient that has a predetermined minimum score for a consultation with said referring physician's office;

completing the medical treatment specific physician consultation questionnaire record, wherein said patient visits said referring physician's office and personnel from said referring physician's office accesses said medical treatment specific physician consultation questionnaire record using a browser connected to said system of said referring physician's office to connect to said server through said network, wherein said personnel completes answers to said medical treatment physician consultation questionnaire record and sends those answers to said server using a browser connected to the system of said referring physician's office to connect to said server through said network, wherein said medical treatment specific physician consultation questionnaire record is updated with those answers and stored on said server;

sending said patient records to said company looking for potential candidates for said specific medical treatment.

8. The computer program product of claim 7, wherein:
said specified information includes the name of the condition to be treated by said specific medical treatment, an Institutional Review Board approved description of said specific medical treatment, said inclusion and exclusion criteria for said potential candidates for said specific medical treatment, patient compensation for said potential candidates for said specific medical treatment, information about said specific medical treatment for referring physicians, and available sites for said specific medical treatment.

9. The computer program product of claim 7, wherein:
said medical treatment specific physician information record contains information about said specific medical treatment including location, specialties, compensation, whether the referring physician has participated in recruiting potential candidates for a related medical treatment or company, benefits for said patient, cost of said specific medical treatment, whether said specific medical treatment is new or a new indication of a known medical treatment, that can be sorted using the computer program product based on input from said referring physician to assist in the search of relevant medical treatment specific physician information records.

10. The computer program product of claim 7 wherein:
said computer program product securely connects said server to said system of said referring physician's office, wherein said computer program product connects to said patient database and transfers patient records from said patient database to said server.

11. A system for matching patients with a specific medical treatment comprising:
a server connected to a network;
a data storage device located on said server;
computer executable software code and a database stored on said storage device;
a system of a company looking for potential candidates for a specific medical treatment, wherein said company provides specified information about said specific medical treatment over said network which is stored in said database, wherein said specified information about said specific medical treatment is determined by said computer executable software code;
computer executable software code stored on said storage device and executed on said server that creates a medical treatment specific query record based on said specified information about said specific medical treatment that includes inclusion and exclusion criteria, a medical treatment specific patient screening survey record based on said specified information about said specific medical treatment, a medical treatment specific physician consultation questionnaire record based on said specified information about said specific medical treatment, a medical treatment specific patient information record based on said specified information about said specific medical treatment, and a medical treatment specific physician information record based on said specified information about said specific medical treatment;

a system of a referring physician's office connected to said network that includes a patient database and a browser, wherein said system is used to review and select a specific medical treatment specific physician information record, and wherein said medical treatment specific physician consultation questionnaire record is updated using said browser connected to said system to connect to said server through said network, wherein personnel from said referring physician's office completes answers to said medical treatment specific physician consultation questionnaire record and sends those answers to said server using a browser connected to said system of said referring physician's office to connect to said server through said network, wherein said medical treatment specific physician consultation questionnaire record is updated and stored in said database;

an applet from said server, wherein said applet runs in said browser, connects to said patient database, and accesses said medical treatment specific query record relating to said selected medical treatment, wherein said applet uses said medical treatment specific query record to query said patient database, wherein said query compares patient records in said patient database with said inclusion and exclusion criteria of said specific medical treatment, returning said patient records from said patient database that match said inclusion and exclusion criteria of said specific medical treatment through said network to said server and storing said patient records in said database;

computer executable software code stored on said storage device and executed on said server that compares said patient records with said medical treatment specific patient screening survey record and said medical treatment specific physician consultation questionnaire record and completes fields in said medical treatment specific patient screening survey record and said medical treatment specific physician consultation questionnaire record that match information from said patient records;

an interactive voice response system connected to said server to which a patient associated with said patient records completes said medical treatment specific patient screening survey record, wherein said interactive voice response system accesses said medical treatment specific patient screening survey record and asks said patient unmatched questions from said medical treatment specific patient screening survey record, wherein said patient answers said unmatched questions and said answers are sent through said interactive voice response system to said server, wherein said medical treatment specific patient screening survey record and said medical treatment specific physician consultation questionnaire record are updated and stored in said database;

computer executable software code stored on said storage device and executed on said server that scores answers in said medical treatment specific patient screening survey record and schedules said patient that has a predetermined minimum score for a consultation with said referring physician's office; and computer executable software code stored on said storage device and executed on said server that sends said patient records to said company looking for potential candidates for said specific medical treatment.

12. The system according to claim 11 wherein:
said specified information includes a name of a condition to be treated by said specific medical treatment, an Institutional Review Board approved description of said specific medical treatment, inclusion and exclusion criteria for said potential candidates for said specific medical treatment, patient compensation for said potential candidates for said specific medical treatment, information about said specific medical treatment for referring physicians, and available sites for said specific medical treatment.

13. The system according to claim 11 wherein:
said medical treatment specific physician information record contains information about said specific medical treatment including location, specialties, compensation, whether the physician has participated in recruiting potential candidates for a related medical treatment or company, benefits for said potential patient, cost of said specific medical treatment, whether said specific medical treatment is new or a new indication of a known medical treatment, that can be sorted using said computer executable software code based on input from said physician to assist in the search of relevant medical treatment specific physician information records.

14. The system according to claim 11 further comprising:
a system of a patient that includes a browser that is connected to said network, wherein said patient is presented through said patient's browser said unmatched questions to said medical treatment specific patient screening survey record, wherein said patient then answers said unmatched questions and the answers are sent through said network to said server, wherein said medical treatment specific patient screening survey record and said medical treatment specific physician consultation questionnaire record are updated and stored in said database.

15. A data processing system for identifying candidates for a specific medical treatment, comprising:
a computer server configured to automatically create a medical specific query record that includes inclusion and exclusion criteria for identifying the candidates for the specific medical treatment;
the computer server configured to set up a first network connection configured to establish a secure network communication of the computer server with a patient database residing on a physician's computer system;
the computer server configured to run a query over the secure network connection on the patient database residing on the physician's computer system, wherein the query selects patient records in the patient database that match the inclusion and exclusion criteria, wherein the query retrieves the matching patient records over the secure network connection to the computer server;
the computer server configured to dynamically complete fields in a medical treatment specific patient screening survey record that match with the retrieved patient records, wherein the medical treatment specific patient screening survey record is stored on a database coupled to the computer server;

the computer server configured to dynamically complete fields in a medical treatment specific physician consultation questionnaire record that match with the retrieved patient records, wherein the medical treatment specific physician consultation questionnaire record is stored on the database coupled to the computer server;

the computer server configured to communicate with a potential candidate associated with the retrieved patient records to retrieve from the potential candidate information to complete any one or more fields within the medical specific patient screening survey record that were not completed from the retrieved patient records thereby producing an updated medical treatment specific patient screening survey record that is stored on the database coupled to the computer server;

the computer server configured to transmit the medical treatment specific physician consultation questionnaire record to the physician's computer system over a second network connection configured to establish communication of the computer server with the physician's computer system to enable a person associated with the physician's computer system to complete any one or more fields within the medical treatment specific physician consultation questionnaire record that were not completed from the retrieved patient records thereby producing an updated medical treatment specific physician consultation questionnaire record; and the computer server configured to transmit over a third network connection an identity of the potential candidate associated with the retrieved patient records.

16. The data processing system as recited in claim 15, wherein the computer server configured to communicate with the potential candidate associated with the retrieved patient records to retrieve from the potential candidate information to complete any one or more fields within the medical specific patient screening survey record that were not completed from the retrieved patient records thereby producing the updated medical treatment specific patient screening survey record that is stored on the database coupled to the computer server further comprises the computer server configured to host a website accessed by the potential candidate over a fourth network connection, wherein the website is configured to receive the information from the potential candidate to complete the any one or more fields within the medical specific patient screening survey record that were not completed from the retrieved patient records.

17. The data processing system as recited in claim 15, further comprising the computer server configured to receive from a third party, over a fourth network connection, the inclusion and exclusion criteria for identifying the candidates for the specific medical treatment.

18. The data processing system as recited in claim 17, wherein the computer server is configured to transmit, to the third party over the third network connection, the identity of the potential candidate, the updated medical treatment specific patient screening survey record, and the updated medical treatment specific physician consultation questionnaire record.

19. The data processing system as recited in claim 15, wherein the computer server is configured to set up the first network connection in response to receipt, from the physician's computer system over a fourth network connection, of a selection of the specific medical treatment.

20. The data processing system as recited in claim 15, further comprising the computer server configured to transmit, over the third network connection, the updated medical specific patient screening survey record and the updated medical treatment specific physician consultation questionnaire record.

* * * * *